US005676963A

United States Patent [19]
Keefer et al.

[11] Patent Number: 5,676,963
[45] Date of Patent: Oct. 14, 1997

[54] IMPLANTS, PROSTHESES, AND STENTS COMPRISING POLYMER-BOUND NITRIC OXIDE/NUCLEOPHILE ADDUCTS CAPABLE OF RELEASING NITRIC OXIDE

[75] Inventors: Larry K. Keefer, Bethesda; Joseph A. Hrabie, Frederick, both of Md.

[73] Assignee: The United States of America as represented by the Department of Health and Human Services, Washington, D.C.

[21] Appl. No.: 417,917

[22] Filed: Apr. 6, 1995

Related U.S. Application Data

[62] Division of Ser. No. 935,565, Aug. 24, 1992, Pat. No. 5,405,919.

[51] Int. Cl.[6] .................. A61L 27/00; C08K 5/22; C08F 8/30
[52] U.S. Cl. .................. 424/423; 424/422; 424/426
[58] Field of Search .................. 424/78.08, 423, 424/426

[56] References Cited

U.S. PATENT DOCUMENTS

| | | | |
|---|---|---|---|
| 3,153,094 | 10/1964 | Reilly | 564/112 |
| 4,265,714 | 5/1981 | Nolan et al. | 204/1.003 |
| 4,482,533 | 11/1984 | Keith | 421/28 |
| 4,638,079 | 1/1987 | Inskip et al. | 560/4 |
| 4,708,854 | 11/1987 | Grinstead | 423/235 |
| 4,921,683 | 5/1990 | Bedell | 423/235 |
| 4,952,289 | 8/1990 | Ciccone et al. | 204/129 |
| 4,954,526 | 9/1990 | Keefer | 514/611 |
| 4,985,471 | 1/1991 | Ohta et al. | 522/27 |
| 5,039,705 | 8/1991 | Keefer et al. | 514/200 |
| 5,087,631 | 2/1992 | Shaffer et al. | 514/342 |
| 5,087,671 | 2/1992 | Loeppky et al. | 525/328.2 |
| 5,094,815 | 3/1992 | Conboy et al. | 422/52 |

FOREIGN PATENT DOCUMENTS

| | | |
|---|---|---|
| PCT/US89/02611 | 6/1989 | European Pat. Off. . |
| 0 425 154 A1 | 10/1990 | European Pat. Off. . |
| 211 789 | 7/1984 | Germany . |

OTHER PUBLICATIONS

Chem. Letters Kobayashi et al. 1976 vol. 11 pp. 1181–1186.
Jones, "Metastable Polymers of the Nitrogen Oxides. 2. Open-Chain Polymers of the Nitric Oxide Dimers and of Nitrous Oxide: A MNDO/AM1 Study," *J. Phys. Chem.*, 96, 594–603 (1992).
1991 Article by Maragos, et al., Complexes of NO with Nucleophiles as Agents for the Controlled Biological Release of Nitric Oxide. Vasorelaxant Effects, *J. Med. Chem.*, 34, 3242–3247.
1990 Article by Myers, et al., Vasorelaxant Propeties of the Endothelium–Derived Relaxing Factor more closely Resemble S–Nitrosocystein Than Nitric Oxide, *Nature*, vol. 345.
1989 Article by Ignarro, Endothelium–Derived Nitric Oxide: Actions and Properties, *The FASEB Journal*, vol. 3, Jan.
1988 Article by DeFeudis, Endothelium–Dependent Vasorelaxation—A New Basis for Developing Cardiovascular Drugs, *Drugs of Today*, vol. 24, No. 2, pp. 103–115.
1987 Article by Palmer, et al., Nitric Oxide Release Accounts for the Biological Activity of Endothelium–Derived Relaxing Factor, *Nature*, vol. 327 11, Jun.
1987 Article by Kruszyna, et al., Red Blood Cells Generate Nitric Oxide from Directly Acting, Nitrogenous Vasodilators, *Toxicol. Appl. Pharmacol.*, 91, 429–438.
1986 Article by Trissel, Intravenous Infusion Solutions, Handbook on *Injectable Drugs*, Fourth Addition.

(List continued on next page.)

*Primary Examiner*—Peter F. Kulkosky
*Attorney, Agent, or Firm*—Leydig, Voit & Mayer, Ltd.

[57] ABSTRACT

Implants, prostheses, and stents comprising a polymeric composition capable of releasing nitric oxide including a polymer and a nitric oxide-releasing $N_2O_2^-$ functional group bound to the polymer.

17 Claims, 2 Drawing Sheets

OTHER PUBLICATIONS

1984 Article by Furchgott, The Role of Endothelium in the Responses of Vascular Smooth Muscle to Drugs, Ann. Rev. Pharmacol, Toxicol, 24:175–97.

1982 Article by DeLuca, et al., Parenteral Drug–Delivery Systems, *Pharmaceutics and Pharmacy Practice*.

1982 Article by Hansen, et al., N–Nitrosation of Secondary Amines by Nitric Oxide Via the 'Drago Complex', *IARC Sci.*, Publ. No. 41 pp. 21–29.

1981 Article by Ignarro, et al., Mechanism of Vascular Smooth Muscle Relaxation by Organic Nitrates, Nitrites, Nitroprusside and Nitric Oxide: Evidence for the Involvement of S–Nitrosothiols as Active Intermediates, *J. Pharmacol. Exp. Ther.*, 218, 739–749.

1977 Article by Lutz, et al., Isolation of Trioxodinitrato (II) Complexes of Some First Row Transition Metal Ions, *J.C.S. Chem. Comm.*.

1977 Article by Nakanishi, et al., Participation of Hydrocarbons in the Photodimerization of 3, 4–Dichlorocinnamic Acid, *J.C.S. Chem. Comm.*.

1963 Article by Longhi, et al., Metal–Containing Compounds of the Anion $(C_2H_5)_2NN_2O_2-$, *Insrg. Chem.*, vol. 2, Feb..

1962 Article by Drago, Reactions of Nitrogen (II) Oxide, *Advances In Chemistry Series*, No. 36.

1961 Article by Drago, et al., The Reaction of Nitrogen (II) Oxide with Various Primary and Secondary Amines, *Journal of Amer. Chem. Soc.*, vol. 83, Apr. 20.

1990 Article by Garg, et al., Nitric Oxide–Generating Vasodilators Inhibit Mitogenesis and Proliferation of Balb/C3T3 Fibroblasts By A Cyclic GMP–Independent Mechanism, *Biochem. and Biophys. Res. Comm.*, 171, 474–479.

1988 Article by Hibbs, Jr., et al., Nitric Oxide: A Cytotoxic Activated Macrophage Effector Molecule, *Biochem. and Biophys. Res. Comm.*, 157, 87–94.

1981 Article by Holford, et al., Understanding the Dose–Effect Relationship: Clinical Application of Pharmacokinetic–Pharmacodynamic Models, *Clinical Pharmacokinetics*, 6, 429–453.

1990 Article by Ignarro, Nitric Oxide. A Novel Signal Transduction Mechanism for Transcellular Communication, *Hypertension (Dallas)*, 16, 477–483.

1990 Article by Ignarro, Biosynthesis and Metabolism of Endothelium–Derived Nitric Oxide, *Annu. Rev. Pharmacol. Toxicol.*, 30, 535–560.

1985 Article by Ignarro, et al., The Pharmacological and Physiological Role of Cyclic GMP in Vascular Smooth Muscle Relaxation, *Annu. Rev. Pharmacol. Toxicol.*, 25, 171–191.

1989 Article by Kuhn, et al., Endothelium–Dependent Vasodilatation in Human Epicardial Coronary Arteries: Effect of Prolonged Exposure to Glycerol Trinitrate or SIN–1, *J. Cardiovasc. Pharmacol.*, 14 (Suppl. 11), S47–S54.

1990 Marletta, et al., Unraveling the Biological Significance of Nitric Oxide, *BioFactors*, 2, 219–225.

1991 Smith, et al., Nitroprusside: A Potpourri of Biologically Reactive Intermediates, *Biological Reactive Intermediates IV. Molecular and Cellular Effects and Their Impact on Human Health* (Witmer, et al., eds.), Advances in Experimental Medicine and Biology, vol. 283 (Plenum Press, pp. 365–369).

1989 Stuehr, et al., Nitric Oxide: A Macrophage Product Responsible for Cytostasis and Respiratory Inhibition in Tumor Target Cells, *J. Exp. Med.*, 169, 1543–1555.

1977 WHO Task Group on Environmental Health Criteria for Oxides of Nitrogen, *Oxides of Nitrogen*, Environmental Health Criteria 4 (World Health Organization: Geneva).

1990 Article by Wilcox, et al., Effect of Cyanide on the Reaction of Nitroprusside with Hemoglobin: Relevance to Cyanide Interference With the Biological Activity of Nitroprusside, *Chem. Res. Toxicol.*, 3, 71–76.

1992 Article by Stamler, et al., S–Nitrosylation of Proteins With Nitric Oxide: Synthesis and Characterization of Biologically Active Compounds, *Proc. Natl. Acad. Sci., USA*, vol. 89, pp. 444–448, Jan..

1992 Article by Smith, et al., Complex Contractile Patterns in Canine Colon Produced by Spontaneous Release of Nitric Oxide, *Gastroenterology*, vol. 102, No. 4 Part 2, Apr..

1991 Article by Jones, Metastable Polymers of the Nitrogen Oxides. 1. Open Chain Nitric Oxide Analogues of Polythlazyl: A MNDO/AM1 Study, *J. Phys. Chem.*, 95, 2588–2595.

1981 Article by Middleton, et al., Further Studies on the Interaction of Nitric Oxide With Transition–Metal Alkyls, *J.C.S. Dalton*, pp. 1898–1905, Feb. 6.

1989 Article by Bonakdar, et al., Continuous–Flow Performance of Carbon Electrodes Modified With Immobilized Fe(II)/Fe(III) Centers, *Calanta*, vol., 36, No. 1/2, pp. 219–225.

1992 Article by Park, et al., Controlled Protein Release from Polyethyleneimine–Coated Poly (L–lactic Acid)/Pluronic Blend Matrices, *Pharmaceutical Research*, vol. 9, No. 1.

1932 Uber Reaktionen und Eigenschaften des Stickoxyds und seiner Verbindungen, II. Mitteil: Zur Kenntnis der Salze Der stickoxyd–schwefligen Saure, Heinz Gehlen, *Aus D. Chem. Institut D. Universitat Konigsberg* I. PR., Eingegaugen am 1. Juni.

1932 Der Raman–Effekt als Grundlage einer organischem Spektralanalyse (I. Mitteil.), Birchkenbach, et al., *Aus D. Chem. Institut D., Betgakademie Clausthal*, Eingegaugen am 9, Juni.

1987 Synthesis of 1–Alkoxy–3,3–Dialkyltriazene 2–Oxides from Alkoxyamines and Nitrosoamines, Artsybasheva, et al., A.A. Zhdanov Leningrad State University, Translated from Zhurhal Organicheskoi Khimii, vol. 28, No. 6, pp. 1168–1173, Jun., Original article submitted May 28, 1986.

IMPLANTS, PROSTHESES, AND STENTS COMPRISING POLYMER-BOUND NITRIC OXIDE/NUCLEOPHILE ADDUCTS CAPABLE OF RELEASING NITRIC OXIDE

This is a divisional of application Ser. No. 07/935,565, filed on Aug. 24, 1992, now U.S. Pat. No. 5,405,919.

BACKGROUND OF THE INVENTION

The present invention relates to compositions comprising a nitric oxide/nucleophile adduct capable of releasing nitric oxide. In particular, the present invention relates to compositions comprising nitric oxide/nucleophile adducts which are bound to a polymer and which release nitric oxide in a physiological environment, to pharmaceutical compositions, including implants, patches and the like, incorporating the polymer-bound nitric oxide/nucleophile adduct compositions, and to methods of treating biological disorders with polymer-bound nitric oxide/nucleophile adduct compositions.

Nitric oxide (NO) has recently been implicated in a variety of bioregulatory processes, including normal physiological control of blood pressure, macrophage-induced cytostasis and cytotoxicity, and neurotransmission (Moncada et al., "Nitric Oxide from L-Arginine: A Bioregulatory System," *Excerpta Medica*, International Congress Series 897 (Elsevier Science Publishers B.V.: Amsterdam, 1990); Marletta et al., "Unraveling the Biological Significance of Nitric Oxide," *Biofactors*, 2, 219–225 (1990); Ignarro, "Nitric Oxide. A Novel Signal Transduction Mechanism for Transcellular Communication," *Hypertension (Dallas)*, 16, 477–483 (1990)). A number of compounds have been developed which are capable of delivering nitric oxide, including compounds which release nitric oxide upon being metabolized and compounds which release nitric oxide spontaneously in aqueous solution.

Those compounds which release nitric oxide upon being metabolized include the widely used nitrovasodilators glyceryl trinitrate and sodium nitroprusside (Ignarro et al., *J. Pharmacol. Exp. Ther.*, 218, 739–749 (1981); Ignarro, *Annu. Rev. Pharmacol. Toxicol.*, 30, 535–560 (1990); Kruszyna et al., *Toxicol. Appl. Pharmacol.*, 91, 429–438 (1987); Wilcox et al., *Chem. Res. Toxicol.*, 3, 71–76 (1990). Another compound, S-nitroso-N-acetylpenicillamine, has been reported to release nitric oxide in solution and to be effective at inhibiting DNA synthesis (Garg et al., *Biochem. and Biophys. Res. Comm.*, 171, 474–479 (1990)).

Numerous nitric oxide-nucleophile complexes have been described, e.g., Drago, *ACS Adv. Chem. Ser.*, Vol. 36, p. 143–149 (1962). See also Longhi and Drago, *Inorg. Chem.* 2 85, (1963). Some of these complexes are known to evolve nitric oxide on heating or hydrolysis, e.g., Maragos et al., *J. Med. Chem.* 34, 3242–3247, 1991.

The cytostatic effect of nitric oxide solutions on tumor cells in vitro has been demonstrated. In particular, it has been shown that solutions of nitric oxide inhibit DNA synthesis and mitochondrial respiration of tumor cells in vitro (Hibbs et al., *Biochem. and Biophys. Res. Comm.*, 157, 87–94 (1988); Stuehr et al., *J. Exp. Med.*, 169, 1543–1555 (1989)).

Endothelium-derived relaxing factor (EDRF) is a labile humoral agent which is part of a cascade of interacting agents involved in the relaxation of vascular smooth muscle. EDRF is thus important in the control of vascular resistance to blood flow and in the control of blood pressure. Some vasodilators act by causing EDRF to be released from endothelial cells. (See Furchgott, Ann. Rev. Pharmacol. Toxicol. 24., 175–197, 1984.) In 1987, Palmer et al., presented evidence that EDRF is identical to the simple molecule, nitric oxide, NO (Nature 317, 524–526, 1987), though more recently, that conclusion has been challenged (Myers et al., Nature, 345, 161–163, 1990).

Nitric oxide in its pure form, however, is a highly reactive gas having limited solubility in aqueous media (WHO Task Group on Environmental Health Criteria for Oxides of Nitrogen, *Oxides of Nitrogen*, Environmental Health Criteria 4 (World Health Organization: Geneva, 1977)). Nitric oxide, therefore, is difficult to introduce reliably into most biological systems without premature decomposition.

The difficulty in administering nitric oxide can be overcome in some cases by administering nitric oxide pharmacologically in prodrug form. The compounds glyceryl trinitrate and sodium nitroprusside are relatively stable but release nitric oxide only on redox activation (Ignarro et al., *J. Pharmacol. Exp. Ther.*, 218, 739–749 (1981); Ignarro, *Annu. Rev. Pharmacol. Toxicol.*, 30, 535–560 (1990); Kruszyna et al., *Toxicol. Appl. Pharmacol.*, 91, 429–438 (1987); Wilcox et al., *Chem. Res. Toxicol.*, 3, 71–76 (1990)). While this feature may be an advantage in some applications, it can also be a significant liability, as in the development of tolerance to glyceryl trinitrate via the exhaustion of the relevant enzyme/cofactor system (Ignarro et al., *Annu. Rev. Pharmacol. Toxicol.*, 25, 171–191 (1985); Kuhn et al., *J. Cardiovasc. Pharmacol.*, 14. (Suppl. 11), S47–S54 (1989)) and toxicity from metabolically produced cyanide during prolonged administration of nitroprusside (Smith et al., "A Potpourri of Biologically Reactive Intermediates" in *Biological Reactive Intermediates IV. Molecular and Cellular Effects and Their Impact on Human Health* (Witmer et al., eds.), Advances in Experimental Medicine and Biology Volume 283 (Plenum Press: New York, 1991), pp. 365–369).

Evidence that nitric oxide is released from the endothelial cells and is responsible for the relaxation of the vascular smooth muscle, and hence the control of blood pressure, has resulted in the development of artificial agents that can deliver nitric oxide in vivo. A very important class of such agents is the nitric oxide-nucleophile complexes. Recently, a method for treating cardiovascular disorders in a mammal with certain nitric oxide-nucleophile complexes has been disclosed, e.g. in U.S. Pat. No. 4,954,526. These compounds contain the anionic $N_2O_2^-$ group or derivatives thereof. See also, Maragos et al., J. Med. Chem. 34, 3242–3247, 1991. Many of these compounds have proven especially promising pharmacologically because, unlike nitrovasodilators such as nitroprusside and nitroglycerin, they release nitric oxide without first having to be metabolized. The only other series of drugs currently known to be capable of releasing nitric oxide purely spontaneously is the S-nitrosothiol series, compounds of structure R-S-NO (Stamler et al., Proc. Natl. Acad. Sci. U.S.A. 89, 444–448, 1992); however, the R-S-NO→NO reaction is kinetically complicated and difficult to control (Morley et al., submitted). The $N_2O_2^-$ containing compounds are thus unique among drugs currently known in that they decompose via a cleanly first order reaction to provide doses of nitric oxide that can be predicted, quantified, and controlled. See, e.g., Maragos et al., J. Med. Chem. 34, 3242–3247, 1991.

Nitric oxide/nucleophile complexes which release nitric oxide in aqueous solution are also disclosed in U.S. Pat. No. 5,039,705, as well as in pending U.S. Pat. Nos. 5,212,204 (filed Oct. 18, 1989), 5,155,137 (filed Sep. 20, 1990), 5,208,233 (filed Aug. 12, 1991), application Ser. No. 07/764, 908 (filed Sep. 24, 1991) now abandoned, and 5,384,675

(filed Mar. 27, 1992), as being useful cardiovascular agents (see also Maragos et al., *J. Med. Chem.*, 34, 3242–3247 (1991)).

Despite the promise of the nitric oxide/nucleophile adducts that have been investigated, their pharmacological application has been limited by their tendency to distribute evenly throughout the medium. Such even distribution is a great advantage in many research applications, but tends to compromise their selectivity of action. Another limitation to the application of these nitric oxide/nucleophile adducts is their propensity for relatively rapid release of nitric oxide which may necessitate frequent dosing to achieve a prolonged biological effect. Thus there remains a need for nitric oxide-releasing compositions which are capable of concentrating the effect of the nitric oxide release to a situs of application and for which nitric oxide release may be controlled for effective dosing.

It is therefore a principal object of the present invention to provide a composition which includes a nitric oxide/nucleophile adduct whose action can be localized to enhance the selectivity of nitric oxide release. Another object of the invention is to provide a composition which includes a nitric oxide/nucleophile adduct whose release of nitric oxide can be controlled to effect efficient dosing for a prolonged biological effect. A further object of the present invention is to provide compositions including nitric oxide/nucleophile adducts capable of releasing nitric oxide wherein the nitric oxide/nucleophile adduct is associated with a polymer. These and other objects and advantages of the present invention, as well as additional inventive features, will be apparent from the description of the invention provided herein.

BRIEF SUMMARY OF THE INVENTION

The present invention provides a composition capable of releasing nitric oxide which includes a nitric oxide-releasing $N_2O_2^-$ functional group bound to a polymer. By "bound to a polymer," it is meant that the $N_2O_2^-$ functional group is associated with, part of, incorporated with or contained within the polymer matrix physically or chemically. Physical association or bonding of the $N_2O_2^-$ functional group to the polymer may be achieved by coprecipitation of the polymer with a nitric oxide/nucleophile complex as well as by covalent bonding of the $N_2O_2^-$ group to the polymer. Chemical bonding of the $N_2O_2^-$ functional group to the polymer may be by, for example, covalent bonding of the nucleophile moiety of the nitric oxide/nucleophile adduct to the polymer such that the nucleophile residue to which the $N_2O_2^-$ group is attached forms part of the polymer itself, i.e., is in the polymer backbone or is attached to pendant groups on the polymer backbone. The manner in which the nitric oxide-releasing $N_2O_2^-$ functional group is associated, part of, or incorporated with or contained within, i.e., "bound," to the polymer is inconsequential to the present invention and all means of association, incorporation and bonding are contemplated herein.

The present invention also provides a pharmaceutical composition which includes a pharmaceutically acceptable carrier and a polymer having a nitric oxide-releasing $N_2O_2^-$ functional group bound to said polymer. The polymer-bound nitric oxide-releasing $N_2O_2^-$ functional group compositions of the present invention may themselves function as a pharmaceutical composition, as, for example, when the polymer-bound composition is in the form of an implant, stent, patch, or the like.

The invention further provides a method of treating biological disorders in which dosage with nitric oxide would be beneficial which comprises administering a composition comprising a polymer and a nitric oxide-releasing $N_2O_2^-$ functional group bound to said polymer in an amount sufficient to release a therapeutically effective amount of nitric oxide.

DETAILED DESCRIPTION OF THE PREFERRED EMBODIMENTS

Figure 1:
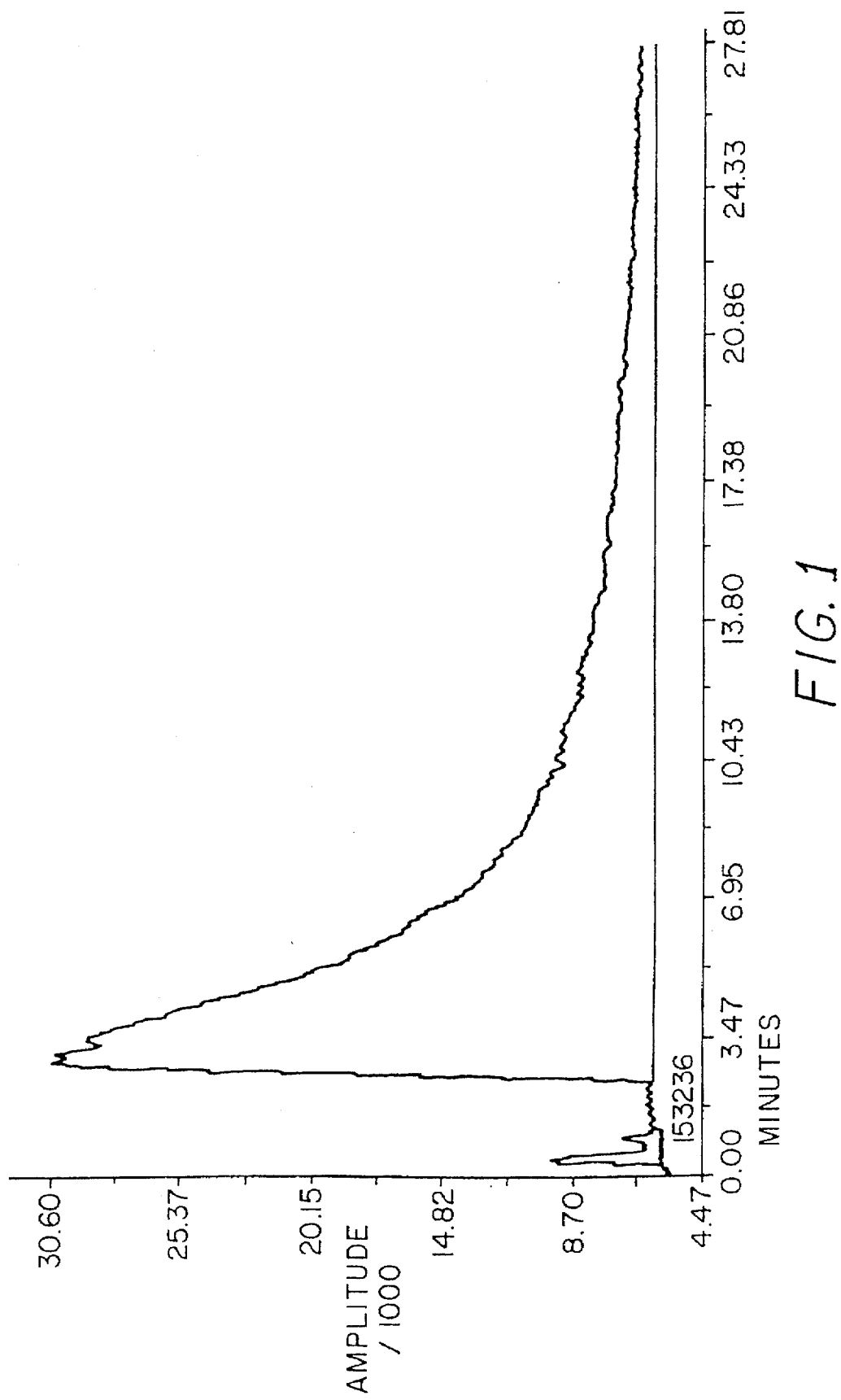
FIG. 1 is the chemiluminescence detector response to nitric oxide generated from the polymer-bound nitric oxide-releasing $N_2O_2^-$ functional group composition of Example 1 in accordance with the invention.

The present invention is predicated on the discovery that useful pharmacological agents can be provided by incorporating nitric oxide-releasing $N_2O_2^-$ functional groups into a polymeric matrix. Accordingly, the $N_2O_2^-$ functional group is "bound to the polymer" as that term has been defined herein. It has been discovered that incorporation of the $N_2O_2^-$ functional group into a polymeric matrix provides a polymer-bound nitric oxide/nucleophile adduct composition that can be applied with specificity to a biological site of interest. Site specific application of the polymer-bound adduct composition enhances the selectivity of action of the nitric oxide releasing $N_2O_2^-$ functional group. If $N_2O_2^-$ functional groups attached to the polymer are necessarily localized, then the effect of their nitric oxide release will be concentrated in the tissues with which they are in contact. If the polymer is soluble, selectivity of action can still be arranged, for example, by attachment to or derivatization of an antibody specific to the target tissue. Similarly, attachment of $N_2O_2^-$ groups to small peptides that mimic the recognition sequences of ligands for important receptors provides localized concentrated effect of nitric oxide release, as would attachment to oligonucleotides capable of site-specific interactions with target sequences in a nucleic acid.

Additionally, incorporation of the $N_2O_2^-$ functional group into a polymer matrix can reduce the propensity of the nitric oxide/nucleophile adduct for the relatively rapid release of nitric oxide. This prolongs the release of nitric oxide by the $N_2O_2^-$ functional group, and allows for efficient dosing to achieve a desired biological effect so the frequency of dosing can be reduced.

While not being bound to any particular theory, it is believed that longevity of nitric oxide release in the polymer-bound nitric oxide/nucleophile adduct compositions of the present invention is to be attributed both to the physical structure of the composition and to electrostatic effects. Thus, it is believed that if the polymer is an insoluble solid, $N_2O_2^-$ groups near the surface of the particle should be available for rapid release while those that are more deeply imbedded are sterically shielded, requiring more time and/or energy for the nitric oxide to work its way into the medium. Unexpectedly, it has been found that increasing positive charge in the vicinity of an $N_2O_2^-$ functional group also tends to increase the halflife of nitric oxide generation. The mechanism of this rate retardation may be attributable simply to repulsive electrostatic interactions, i.e., increasing the number of $H^+$-repelling positive charges in the vicinity of the $N_2O_2^-$ groups inhibits attack of positively charged $H^+$ ions on the $N_2O_2^-$ functional group and slows the rate of its $H^+$- catalyzed decomposition. For example, by attaching amino groups to the polymeric support that are capable of forming the nitric oxide-releasing $N_2O_2^-$ functional group on reaction with nitric oxide, partially converted structures can be produced on less-than-exhaustive treatment with nitric oxide that after exposure to water contain a large number of positively charged ammonium centers surrounding the $N_2O_2^-$ group that electrostatically inhibit the approach of $H^+$ ions capable of initiating nitric oxide loss from the nitric oxide releasing $N_2O_2^-$ functional group.

The nitric oxide-releasing $N_2O_2^-$ functional groups that are bound to the polymer generally are capable of releasing nitric oxide in an aqueous environment spontaneously upon contacting an aqueous environment, i.e., they do not require activation through a redox reaction or electron transfer such as is required for glyceryl trinitrate and sodium nitroprusside. Some of the nitric oxide/nucleophile complexes useful in the context of the present invention do require activation by particular means, but only as necessary to free the nitric oxide releasing $X[N(O)NO]^-$ group in the vicinity of the particular cells of interest. As an example, covalent attachment of a protecting group to the anionic $[N(O)NO]^-$ function provides a means of postponing nitric oxide release until the molecule reaches an organ capable of metabolically removing the protecting group. By choosing a protecting group that is selectively cleaved by enzymes specific to a tumor, biological disorder, cell, or tissue of interest, for example, the action of the nitric oxide/nucleophile complex can be targeted to maximize the desired effect. While the polymer-bound nitric oxide releasing compositions of the present invention are capable of releasing nitric oxide in an aqueous solution, such a compound preferably releases nitric oxide under physiological conditions.

The nitric oxide releasing $N_2O_2^-$ functional group is preferably a nitric oxide/nucleophile adduct, e.g., a complex of nitric oxide and a nucleophile, most preferably a nitric oxide/nucleophile complex which contains the anionic moiety $X[N(O)NO]^-$, where X is any suitable nucleophile residue. The nucleophile residue is preferably that of a primary amine (e.g., $X=(CH_3)_2CHNH$, as in $(CH_3)_2CHNH[N(O)NO]Na$), a secondary amine (e.g., $X=(CH_3CH_2)_2N$, as in $(CH_3CH_2)_2N[N(O)NO]Na$), a polyamine (e.g., X=spermine, as in the zwitterion $H_2N(CH_2)_3NH_2^+(CH_2)_4N[N(O)NO]^-(CH_2)_3NH_2$, or X=3-(n-propylamino)propylamine, as in the zwitterion $CH_3CH_2CH_2N[N(O)NO]^-CH_2CH_2CH_2NH_3^+$), or oxide (i.e., $X=O^-$, as in $NaO[N(O)NO]Na$), or a derivative thereof. Such nitric oxide/nucleophile complexes are stable solids and are capable of delivering nitric oxide in a biologically usable form at a predictable rate.

The nucleophile residue is preferably not an entity such as that of sulfite (e.g., $X=SO_3^-$, as in $NH_4O_3S[N(O)NO]NH_4$) even though the complex is a stable compound, since it is capable of releasing nitric oxide in an aqueous environment only under harsh, nonphysiological conditions.

Other suitable nitric oxide/nucleophile complexes include those having the following formulas:

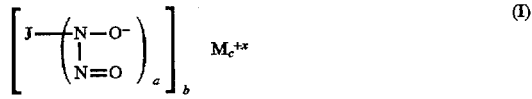
(I)

wherein J is an organic or inorganic moiety, preferably a moiety which is not linked to the nitrogen of the $N_2O_2^-$ group through a carbon atom, $M^{+x}$ is a pharmaceutically acceptable cation, where x is the valence of the cation, a is 1 or 2, and b and c are the smallest integers that result in a neutral compound, preferably such that the compound is not a salt of alanosine or dopastin, as described in U.S. Pat. No. 5,213,204 and incorporated herein by reference;

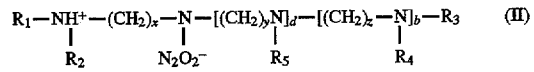
(II)

wherein b and d are the same or different and may be zero or one, $R_1$, $R_2$, $R_3$, $R_4$, and $R_5$ are the same or different and may be hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, and x, y, and z are the same or different and are integers from 2 to 12, as described in U.S. Pat. No. 5,155,137 and

(III)

wherein B is

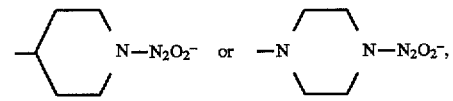

$R_6$ and $R_7$ are the same or different and may be hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, f is an integer from 0 to 12, with the proviso that when B is the substituted piperazine moiety

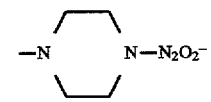

then f is an integer from 2 to 12, as described in U.S. Pat. No. 5,155,137 and incorporated by reference;

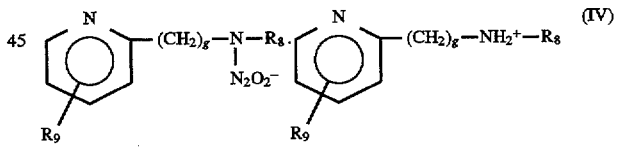
(IV)

wherein $R_8$ is hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, $R_9$ is hydrogen or a $C_1-C_{12}$ straight or branched chain alkyl, and g is 2 to 6, as described in U.S. Pat. No. 5,155,137 and incorporated by reference

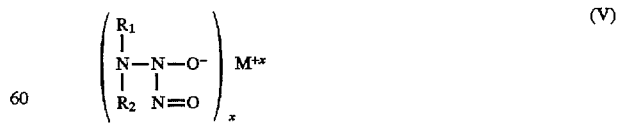
(V)

wherein $R_1$ and $R_2$ are independently selected from the group consisting of a straight chain or branched chain $C_1-C_{12}$ alkyl group and a benzyl group, with the proviso that no branch occur on the alpha carbon atom, or else $R_1$ and $R_2$ together with the nitrogen atom they are bonded to form a heterocyclic group, preferably a pyrrolidino, piperidino, piperazino or morpholino group, $M^{+x}$ is a pharmaceutically acceptable cation, and x is the valence of the cation, as described in U.S. Pat. No. 5,039,705 and incorporated by reference;

$$K[(M)^{x'}_x(L)_y(R^1R^2N-N_2O_2)_z] \qquad (VI)$$

wherein M is a pharmaceutically acceptable metal, or, where x is at least two, a mixture of two different pharmaceutically acceptable metals, L is a ligand different from $(R^1R^2N-N_2O_2)$ and is bound to at least one metal, $R^1$ and $R^2$ are each organic moieties and may be the same or different (with the proviso that where M is copper, x is one, L is methanol, and y is one, that at least one of $R^1$ or $R^2$ is not ethyl), x is an integer of from 1 to 10, x' is the formal oxidation state of the metal M, and is an integer of from 1 to 6, y is an integer of from 1 to 18, and where y is at least 2, the ligands L may be the same or different, z is an integer of from 1 to 20, and K is a pharmaceutically acceptable counterion to render the compound neutral to the extent necessary, as described in U.S. Pat. No. 5,389,675 and incorporated by reference; and

$$[R-N(H)N(NO)O-]_yX \qquad (VII)$$

wherein R is $C_{2-8}$ lower alkyl, phenyl, benzyl, or $C_{3-8}$ cycoloalkyl, any of which R groups may be substituted by one to three substituents, which are the same or different, selected from the group consisting of halo, hydroxy, $C_{1-8}$ alkoxy, $-NH_2$, $-C(O)NH_2$, $-CH(O)$, $-C(O)OH$, and $-NO_2$, X is a pharmaceutically acceptable cation, a pharmaceutically acceptable metal center, or a pharmaceutically acceptable organic group selected from the group consisting of $C_{1-8}$ lower alkyl, $-C(O)CH_3$, and $-C(O)NH_2$, and y is one to three, consistent with the valence of X, as described in U.S. Pat. No. 4,954,526 and incorporated by reference;

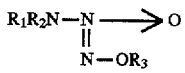

wherein $R_1$ and $R_2$ are independently chosen from $C_{1-2}$ straight chain alkyl, $C_{1-12}$ alkoxy or acyloxy substituted straight chain alkyl, $C_{2-12}$ hydroxy or halo substituted straight chain alkyl, $C_{3-12}$ branched chain alkyl, $C_{3-12}$ hydroxy, halo, alkoxy, or acyloxy substituted branched chain alkyl, $C_{3-12}$ straight chain olefinic and $C_{3-12}$ branched chain olefinic which are unsubstituted or substituted with hydroxy, alkoxy, acyloxy, halo or benzyl, or $R_1$ and $R_2$ together with the nitrogen atom to which they are bonded form a heterocyclic group, preferably a pyrrolidino, piperidino, piperazino or morpholino group, and $R_3$ is a group selected from $C_{1-12}$ straight chain and $C_{3-12}$ branched chain alkyl which are unsubstituted or substituted by hydroxy, halo, acyloxy or alkoxy, $C_{2-12}$ straight chain or $C_{3-12}$ branched chain olefinic which are unsubstituted or substituted by halo, alkoxy, acyloxy or hydroxy, $C_{1-12}$ unsubstituted or substituted acyl, sulfonyl and carboxamido; or $R_3$ is a group of the formula $-(CH_2)_n-ON=N(O)NR_1R_2$, wherein n is an integer of 2–8, and $R_1$ and $R_2$ are as defined above; with the proviso that $R_1$, $R_2$ and $R_3$ do not contain a halo or a hydroxy substituent α to a heteroatom, as described in U.S. application Ser. No. 07/764,908 filed Sep. 24, 1991, abandoned.

Any of a wide variety of polymers can be used in the context of the present invention. It is only necessary that the polymer selected is biologically acceptable. Illustrative of polymers suitable for use in the present invention are polyolefins, such as polystyrene, polypropylene, polyethylene, polytetrafluorethylene, polyvinylidene difluoride, polyvinylchloride, derivatized polyolefins such as polyethylenimine, polyethers, polyesters, polyamides such as nylon, polyurethanes, biopolymers such as peptides, proteins, oligonucleotides, antibodies and nucleic acids, starburst dendrimers, and the like.

The physical and structural characteristics of the polymers suitable for use in the present invention are not narrowly critical, but rather will depend on the end use application. It will be appreciated by those skilled in the art that where the polymer-bound nitric oxide/nucleophile adduct compositions of the present invention are intended for topical, dermal, percutaneous, or similar use, they need not be biodegradable. For some uses, such as ingestion or the like, it may be desirable that the polymer of the polymer-bound compositions slowly dissolves in a physiological environment or that it is biodegradable.

The polymer-bound nitric oxide releasing compositions of the present invention will find utility in a wide variety of applications and in a wide variety of forms depending on the biological disorder to be treated. For example, the polymer may itself be structurally sufficient to serve as an implant, patch, stent or the like. Further, by way of illustration, the polymer-bound composition may be incorporated into other polymer matrices, substrates or the like, or it may be microencapsulated, or the like.

The nitric oxide-releasing complexes having $N_2O_2^-$ functional groups, including the compounds described above, may be bound to the polymer support in a number of different ways. For example, the compounds described above may be bound to the polymer by coprecipitation of such compounds with the polymer. Coprecipitation involves, for example, solubilizing both the polymer and the nitric oxide/nucleophile compound and evaporating the solvent.

Alternatively, nitric oxide releasing $N_2O_2^-$ functional groups may be bound to the polymer by formation of a nitric oxide/nucleophile complex of the types and having the formulas of those described above, in situ on the polymer. The $N_2O_2^-$ functional group may be attached to an atom in the backbone of the polymer, or it may be attached to a group pendant to the polymer backbone, or it may simply be entrapped in the polymer matrix. Where the $N_2O_2^-$ functional group is in the polymer backbone, the polymer includes in its backbone sites which are capable of reacting with nitric oxide to bind the nitric oxide for future release. For example, where the polymer is polyethylenimine, the polymer includes nucleophilic nitrogen atoms which react with nitric oxide to form the $N_2O_2^-$ functional group at the nitrogen in the backbone. Where the $N_2O_2^-$ functional group is a group pendant to the polymer backbone, the polymer contains, or is derivatized with, a suitable nucleophilic residue capable of reacting with nitric oxide to form the $N_2O_2^-$ functionality. Reaction of the polymer which contains a suitable nucleophilic residue, or of the suitably derivatized polymer with nitric oxide thus provides a polymer-bound nitric oxide-releasing $N_2O_2^-$ functional group. To form the polymer-bound nitric oxide releasing $N_2O_2^-$ functional group, it is generally preferred to impart a net charge to the polymer near the site on the polymer where the $N_2O_2^-$ functional group is to be formed.

The polymer-bound nitric oxide/nucleophile compositions of the present invention have a wide range of biological utility. In view of the growing awareness that nitric oxide is an especially versatile and important bioeffective species, having been implicated mechanistically in such critical bodily functions as vasorelaxation, neurotransmission and the immunological response (Moncada et al., Pharmacol.

Rev. 43, 109–142, 1991), the compositions of the present invention find utility in applications where nitric oxide release is needed. For example, the polymer-bound nitric oxide releasing $N_2O_2^-$ functional groups may be implanted into neoplastic tissue to arrest tumor growth.

The following are further illustrative of, and not in any way in limitation of, the broad uses and applications of the polymer-bound compositions of this invention. Thus, for example, in view of dramatic but short-lived pulmonary vaso-and bronchodilatory properties exhibited by nitric oxide (Roberts et al., Circulation (Suppl. II) 84:A1279, 1991), administration of polymer-bound nitric oxide/nucleophile adduct compositions into the lungs in aerosolized form may be used in treating a variety of pulmonary disorders. Oral dosage forms for long-lived drugs containing anionic $N_2O_2^-$ functional groups that survive the acid conditions of the stomach may be used for the treatment of hypertension. Since natural, endogenous nitric oxide has been identified as an effector of penile erection (Blakeslee, N.Y. Times, Jan. 9, 1992, page A1), the polymer-bound nitric oxide/nucleophile adduct compositions of the present invention may be incorporated into suitable penile implants, dermal patches or condoms for treatment of impotence in men. The ability of certain monomeric nitric oxide/nucleophile adducts to inhibit platelet aggregation coupled with their demonstrated cytostatic activity allows for an invaluable two-pronged approach to prevention of restenosis following angioplasty; stents fabricated with polymer-bound nitric oxide-releasing $N_2O_2^-$ functional group compositions may be used both to inhibit cell division in areas with damaged endothelium and to prevent adhesion of platelets at these locations as well, minimizing the risk of recurring blockage. With an inverse relationship between generation of nitric oxide by tumor cells and their metastatic potential having been proposed (Radomski et al., Cancer Res. 51, 6073–6078, 1991), polymer-bound nitric oxide/nucleophile compositions may be used to reduce the risk of metastasis in cancer patients. Similarly, it is contemplated that the polymer-bound nitric oxide/nucleophile adduct compositions of the present invention may be used to coat prostheses and medical implants, such as breast implants, prior to surgical connection to the body as a means of reducing the risk of solid state carcinogenlsis associated therewith. With nitric oxide being additionally implicated in gastric motility, neurotransmission, nociception, and other natural roles, the compositions of this invention may be used for those applications as well.

One skilled in the art will appreciate that suitable methods of administering the polymer-bound nitric oxide-releasing $N_2O_2^-$ functional group compositions of the present invention to an animal are available, and, although more than one route can be used to administer a particular composition, a particular route can provide a more immediate and more effective reaction than another route. Pharmaceutically acceptable carriers are also well-known to those who are skilled in the art. The choice of carrier will be determined in part by the particular composition, as well as by the particular method used to administer the composition. Accordingly, there is a wide variety of suitable formulations of the pharmaceutical composition of the present invention.

Formulations suitable for oral administration can consist of (a) liquid solutions, such as an effective amount of the polymer-bound composition dissolved in diluents, such as water or saline, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The polymer-bound nitric oxide-releasing compositions of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to an animal, particularly a human, in the context of the present invention should be sufficient to effect a therapeutic response in the animal over a reasonable time frame. The dose will be determined by the strength of the particular compositions employed and the condition of the animal, as well as the body weight of the animal to be treated. The size of the dose also will be determined by the existence, nature, and extent of any adverse side-effects that might accompany the administration of a particular composition.

The following examples further illustrate the present invention, but do not limit the scope thereof.

EXAMPLES

The preparation and characterization of polymers containing the nitric oxide-releasing $N_2O_2^-$ functional group are illustrated in the following examples:

Example I

This Example illustrates the formation of a polymer containing nitric oxide-releasing $N_2O_2^-$ groups that are attached to nucleophile residues pendant the polymer backbone.

A slurry of 3.0 g chloromethylated polystyrene (1% divinylbenzene; 1.09 mEq C1 per gram; 200–400 mesh; Polysciences, Inc., Warrington, Pa.) in 20 mL n-propyl-1,3-propanediamine was warmed to 60° C. in an oil bath and swirled periodically for 5 days. The polymer was then filtered, washed repeatedly with water then methanol and finally dichloromethane and dried in vacuo for 24 hrs. Elemental analysis showed this material to be 2.21% nitrogen indicating that approximately 80% of the chlorines had been replaced by propylpropanediamino groups. A slurry of 1.0 g of the resulting aminopolystyrene in 50 mL acetonitrile was placed under 5 atmospheres nitric oxide in a Parr apparatus and shaken intermittently for 3 days. This was filtered and dried in vacuo to yield 0.84 g of cream colored polymer. The elemental analysis suggested that approximately one-third of the amino side chains became attached to $N_2O_2^-$ groups under these conditions.

Using the procedure of Maragos et al. (J. Med. Chem. 34, 3242–3247, 1991) it was demonstrated that nitric oxide can be recovered from the polymer described in this Example. The amount of nitric oxide regenerated when the polymer of Example I was treated with acid was measured with a chemiluminescence detector. The solid sample was placed in a reactor vessel, which was then purged continuously with helium such that the effluent gases were swept into a nitric oxide-selective Thermal Energy Analyzer Model 502 (Thermo Electron Corp., Waltham, Mass.). The observed detector response as a function of time is illustrated in FIG. 1. As can be seen, only small amounts of nitric oxide were evolved from the solid itself, but when 2 mL of 10 mM sulfuric acid was injected via a septum, a sudden pulse of nitric oxide appeared. Integration of this apparently first order generation of nitric oxide over time indicated that 11 nmol of nitric oxide was recovered from 1 mg of polymer.

The reaction was repeated using 10 mM phosphate buffer at pH 7.4 in place of the sulfuric acid to verify the slow release of nitric oxide at physiological pH. The chemiluminescence detector showed that nitric oxide was generated very much more slowly.

Example II

This Example illustrates the preparation of a polymer-bound nitric oxide/nucleophile complex by coprecipitation of a monomeric form thereof with a polymer.

One gram of polymer [poly(lactide/glycolide, 50:50) from MediSorb] was dissolved in 2 mL of THF. To the solution was added 300 mg of $[H_2N(CH_2)_2]_2N\text{-}N_2O_2H$, zwitterionic form, and the mixture was stirred under an argon stream to remove solvent slowly until the mixture became too viscous to stir. The mixture was then placed in a vacuum oven (ca 1 mm) at 30° C. for 5 hours to remove the residual solvent. The mixture was finally pressed on a carver press at 20,000 lbs. at 140° F. for 5 minutes. A film of 1"×1" with thickness of 44 mills was thus prepared. Using the procedure described above, nitric oxide was recovered from this polymer on treatment with acid at the rate of 8 nmol/mg.

Example III

This Example illustrates the preparation of a polymer-bound nitric oxide/nucleophile adduct in which the $N_2O_2^-$ group is bound directly to an atom in the polymer backbone.

A slurry of 10.0 g polyethylenimine on silica gel (Aldrich) in 150 mL acetonitrile was stirred for 3 days under a nitric oxide pressure of 75–80 psig. The resulting orange solid was filtered, washed with $CH_3CN$ then ether, and dried in vacuo for 6 h. Using the procedure described above, nitric oxide was recovered from this polymer on treatment with acid at the rate of 3 nmol/mg.

PHARMACOLOGY EXPERIMENT

In the test procedures utilized, thoracic aortic rings from New Zealand White rabbits were suspended in pH 7.4 buffer at 37° C. and a 10 g preload was applied to each. After equilibration for 2 hours, the rings were preconstricted with norepinephrine. The percent relaxation caused by adding the polymer-bound compositions of the present invention to the organ baths at successively increasing concentrations was measured.

Figure 2:
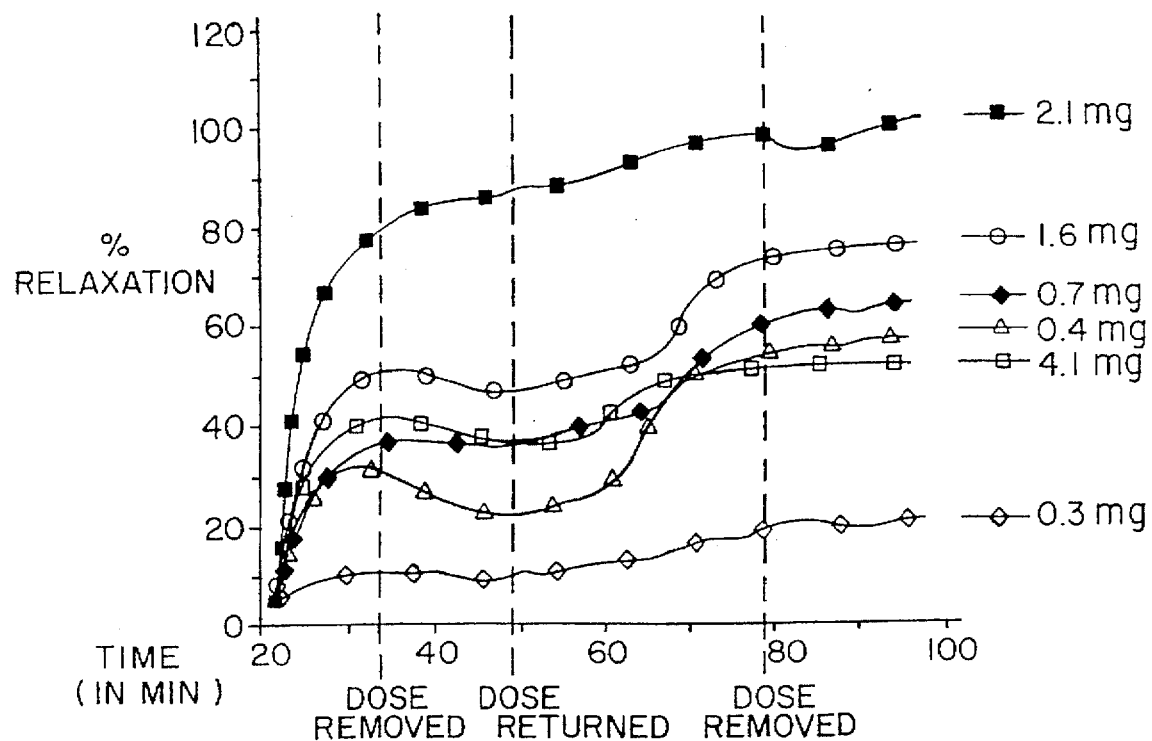
FIG. 2 is a graph illustrating the time course of vascular relaxation with different doses of the polymer-bound nitric oxide-releasing composition of Example 2.

A polymer film as described in Example II was cooled on dry ice and a small piece was sliced off. This was placed onto a piece of weighed filter paper, which was reweighed to determine the amount of material present. The paper was folded to entrap the polymer inside, grasped with a hemostat, and immersed into the 50-ml buffer bath containing the preconstricted aortic ring. As illustrated in FIG. 2, a piece of polymer weighing approximately 0.4 mg induced 30% relaxation in the ring, while 2.1 mg induced 80% relaxation. The data demonstrate that there was a positive response by the organ to the polymer-bound composition of this invention and that the response tended to increase as the dose administered was increased. Thus, the polymer-bound nucleophile/nitric oxide composition has a potent, dose-responsive cardiovascular effect.

The above experiment was repeated with the granular polymer produced in Example III. A similar effect was observed, though it was less potent because this polymer contained fewer NO-releasing $N_2O_2^-$ groups per gram than the polymer of Example II.

Figure 3:
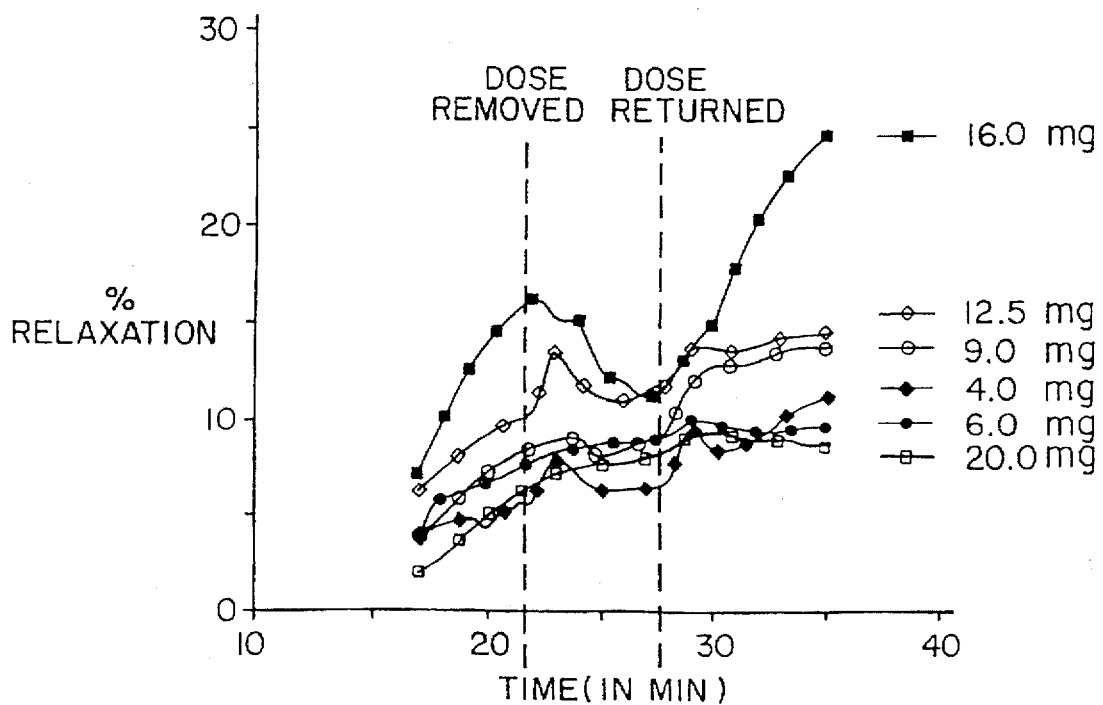
FIG. 3 is a graph illustrating the time course of vascular relaxation with different doses of the polymer-bound nitric oxide-releasing composition of Example 3.

FIG. 3 illustrates the time course of vascular relaxation when different doses of the polymer-bound nitric oxide-releasing composition of Example 3 are first exposed to the aortic ring, causing relaxation, then withdrawn from the organ bath, allowing restriction to occur, then reintroduced into the organ bath, causing the vessel to dilate again. In this experiment, a 16-mg sample of the polymer-bound nitric oxide-releasing composition of Example 3 was immersed into the buffer bath. After 15% relaxation had been achieved, the sample was removed from the bath. Upon removal of the polymer-bound composition, the degree of relaxation fell to approximately 11% over about 5 min. The sample of the polymer-bound composition was then returned to the bath, and a doubling of the degree of relaxation to about 25% was observed.

This experiment illustrates that the pharmacological effects of the polymer-bound nitric oxide/nucleophile composition of the present invention can be modulated as desired by controlling the extent and duration of contact between the polymer and the cells or tissues of interest. This feature is particularly advantageous, for example, to localize the effects of nitric oxide release to a specific target organ or situs.

We claim:

1. An implant comprising a polymer capable of releasing nitric oxiae, said polymer comprising a polymeric backbone selected from the group consisting of a polyolefin, a polyether, a polyester, a polyamide, a polyurethane, a peptide, a polyethyleneimine, and a starburst dendrimer, and at least one nitric oxide-releasing [$N_2O_2$] functional group bound to said polymer, wherein said nitric oxide-releasing [$N_2O_2$] functional group is selected from the group consisting of X-[-N(O)NO] and [N(O)NO-]-X, wherein X is an organic moiety covalently bonded to said [-N(O)NO] or [N(O)NO-], wherein the [-N(O)NO] or [N(O)NO-] group is covalently bonded in said polymer through said organic moiety X, and wherein said implant is adapted to fit a mammalian body.

2. The implant of claim 1, wherein said implant is a breast implant.

3. The implant of claim 1, wherein said implant is a penile implant.

4. The implant of claim 1, wherein the organic moiety of said functional group is part of the polymer backbone.

5. The implant of claim 1, wherein the organic moiety of said functional group is part of a group pendant to said polymer backbone.

6. The implant of claim 1, wherein said polymeric backbone is a polyolefin.

7. The implant of claim 4, wherein said organic moiety X of the group X-[-N(O)NO] is of an amine selected from the group consisting of a primary amine, a secondary amine, a polyamine and derivatives thereof.

8. A prosthesis comprising a polymer capable of releasing nitric oxide, said polymer comprising a polymeric backbone selected from the group consisting of a polyolefin, a polyether, a polyester, a polyamide, a polyurethane, a peptide, a polyethyleneimine, and a starburst dendrimer, and at least one nitric oxide-releasing $[N_2O_2]$ functional group bound to said polymer, wherein said nitric oxide-releasing $[N_2O_2]$ functional group is selected from the group consisting of X-[-N(O)NO] and [N(O)NO-]-X, wherein X is an organic moiety covalently bonded to said [-N(O)NO] or [N(O)NO-], wherein the [-N(O)NO] or [N(O)NO-] group is covalently bonded in said polymer through said organic moiety X, and wherein said prosthesis is adapted to fit a mammalian body.

9. The prosthesis of claim 8, wherein the organic moiety of said functional group is part of the polymer backbone.

10. The prosthesis of claim 8, wherein the organic moiety of said functional group is part of a group pendant to said polymer backbone.

11. The prosthesis of claim 9, wherein said organic moiety X of the group X-[-N(O)NO] is of an amine selected from the group consisting of a primary amine, a secondary amine, a polyamine and derivatives thereof.

12. A stent comprising a polymer capable of releasing nitric oxide, said polymer comprising a polymeric backbone selected from the group consisting of a polyolefin, a polyether, a polyester, a polyamide, a polyurethane, a peptide, a polyethyleneimine, and a starburst dendrimer, and at least one nitric oxide-releasing $[N_2O_2]$ functional group bound to said polymer, wherein said nitric oxide-releasing $[N_2O_2]$ functional group is selected from the group consisting of X-[-N(O)NO] and [N(O)NO-]-X, wherein X is an organic moiety covalently bonded to said [-N (O) NO] or [N(O) NO-], wherein the [-N(O)NO] or [N(O)NO-] group is covalently bonded in said polymer through said organic moiety X, and wherein said prosthesis is adapted to fit a mammalian body.

13. The stent of claim 12, wherein the organic moiety X of said functional group is part of the polymer backbone.

14. The stent of claim 12, wherein the organic moiety of said functional group is part of a group pendant to said polymer backbone.

15. The stent of claim 13, wherein said organic moiety X of the group X-[-N(O)NO] is of an amine selected from the group consisting of a primary amine, a secondary amine, a polyamine and derivatives thereof.

16. The prosthesis of claim 10, wherein said organic moiety X of the group X-[-N(O)NO] is of an amine selected from the group consisting of a primary amine, a secondary amine, a polyamine and derivatives thereof.

17. The stent of claim 14, wherein said organic moiety X of the group X-[-N(O)NO] is of an amine selected from the group consisting of a primary amine, a secondary amine, a polyamine and derivatives thereof.

* * * * *